(12) United States Patent
de la Guardia, Jr. et al.

(10) Patent No.: US 8,950,411 B2
(45) Date of Patent: *Feb. 10, 2015

(54) COMPOSITIONS FOR NEUTRALIZING AND COLORING HAIR AND METHODS THEREOF

(75) Inventors: Mario M. de la Guardia, Jr., Duluth, GA (US); Tony Ray Adair, Daphne, AL (US)

(73) Assignee: Strength of Nature, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/585,074

(22) Filed: Aug. 14, 2012

(65) Prior Publication Data
US 2013/0255712 A1 Oct. 3, 2013

Related U.S. Application Data

(63) Continuation of application No. 10/959,758, filed on Oct. 6, 2004, now Pat. No. 8,256,436, which is a continuation-in-part of application No. 10/654,233, filed on Sep. 2, 2003, now Pat. No. 7,874,299.

(30) Foreign Application Priority Data

Sep. 2, 2004 (ZA) .................................. 2004/7004

(51) Int. Cl.
| | | |
|---|---|---|
| *A61Q 5/00* | (2006.01) | |
| *A61Q 5/10* | (2006.01) | |
| *A61Q 5/06* | (2006.01) | |
| *A61K 8/365* | (2006.01) | |
| *A61Q 5/04* | (2006.01) | |
| *A61K 8/46* | (2006.01) | |
| *A61K 8/04* | (2006.01) | |
| *A61K 8/44* | (2006.01) | |

(52) U.S. Cl.
CPC . *A61K 8/046* (2013.01); *A61Q 5/10* (2013.01); *A61Q 5/065* (2013.01); *A61K 2800/45* (2013.01); *A61K 8/365* (2013.01); *A61Q 5/04* (2013.01); *A61K 8/466* (2013.01); *A61K 8/44* (2013.01); *A61K 8/442* (2013.01)
USPC .......................................... 132/208; 424/70.6

(58) Field of Classification Search
None
See application file for complete search history.

(56) References Cited

U.S. PATENT DOCUMENTS

| | | | |
|---|---|---|---|
| 5,293,885 A | | 3/1994 | Darkwa et al. |
| 6,231,844 B1 | * | 5/2001 | Nambu ..................... 424/70.31 |
| 7,874,299 B2 | | 1/2011 | de la Guardia, Jr. et al. |
| 8,256,436 B2 | | 9/2012 | de la Guardia, Jr. et al. |

FOREIGN PATENT DOCUMENTS

| | | | |
|---|---|---|---|
| BR | PI0403674 | | 5/2005 |
| EP | 260716 | * | 3/1986 |
| WO | WO 93/00882 | * | 1/1993 |
| ZA | 200407004 | | 5/2005 |

OTHER PUBLICATIONS

Office Action from Brazilian PTO issued Mar. 12, 2012 for BR PI0403674-3, which was filed Sep. 2, 2004 (Inventor—Mario M. de la Guardia, Jr.; Applicant—Strength of Nature) (pp. 1-2).
"Declaration of Absence of Access" filed on Jun. 1, 2012 for BR PI0403674-3, which was filed Sep. 2, 2004 (Inventor—Mario de la Guardia, Jr.; Applicant—Strength of Nature)(pp. 1-5).
Request for Continued Examination filed on Feb. 6, 2014 for U.S. Appl. No. 12/972,986, filed Dec. 20, 2010 (Inventor Mario M. de la Guardia, Jr.; Applicant—Strength of Nature). (pp.1-1).
Amendment and Response filed on Feb. 6, 2014 for U.S Appl. No. 12/972,986, filed Dec. 20, 2010 (Inventor Mario M. de la Guardia, Jr.; Applicant—Strength of Nature). (pp. 1-11).
Final Rejection issued Aug. 6, 2013 for U.S Appl. No. 12/972,986, filed Dec. 20, 2010 (Inventor Mario M. de la Guardia, Jr.; Applicant—Strength of Nature). (pp. 1-10).
Amendment and Response filed on Apr. 9, 2013 for U.S Appl. No. 12/972,986, filed Dec. 20, 2010 (Inventor—Mario M. de la Guardia, Jr.; Applicant—Strength of Nature). (pp. 1-11).
Non-Final Rejection issued Oct. 9, 2012 for U.S Appl. No. 12/972,986, filed Dec. 20, 2010 (Inventor—Mario M. de la Guardia, Jr.; Applicant—Strength of Nature). (pp. 1-6).
Response to Election Requirement filed Jul. 23, 2012 for U.S Appl. No. 12/972,986, filed Dec. 20, 2010 (Inventor—Mario M. de la Guardia, Jr.; Applicant—Strength of Nature). (pp. 1-2).
Restriction Requirement issued Mar. 23, 2012 for U.S Appl. No. 12/972,986, filed Dec. 20, 2010 (Inventor—Mario M. de la Guardia, Jr.; Applicant—Strength of Nature). (pp. 1-6).

* cited by examiner

*Primary Examiner* — Jyothsna Venkat
(74) *Attorney, Agent, or Firm* — Ballard Spahr LLP

(57) ABSTRACT

The present invention relates to processes for neutralizing relaxed hair. Still further, the present invention relates to neutralizer compositions for use on relaxed hair. Still further, the present invention relates to a system for neutralizing relaxed hair. Yet further, the invention relates to relaxed hair neutralized by the compositions and methods disclosed herein. The present invention also relates to compositions and methods to simultaneously neutralize and color relaxed hair.

8 Claims, 3 Drawing Sheets

FIGURE 2A: COMPARISONS OF NEUTRALIZER COLORANT COMPOSITIONS AND COMPETITIVE COLORANT PRODUCT

| | Color Mousse | | Color Mousse | Comparative Competitive Products | Color Mousse | Comparative Competitive Products |
|---|---|---|---|---|---|---|
| | After Neutralizing Hair | Comparative Competitive Products After Color Application | After Neutralizing Hair | After Color Application | After Neutralizing Hair | After Color Application |
| By Number of Respondents Rating Scale | Color Intensity | Color Intensity | Ease Of Combing/Tangles | Ease Of Combing/Tangles | Rate Hair Loss/Breakage | Rate Hair Loss/Breakage |
| 10 — A Lot Of Color / Very Easy / A Lot Of Loss | 2 | 3 | 0 | 0 | 0 | 0 |
| 9 | 10 | 5 | 13 | 0 | 0 | 0 |
| 8 | 4 | 0 | 3 | 2 | 0 | 0 |
| 7 | 1 | 0 | 0 | 0 | 0 | 0 |
| 6 | 0 | 0 | 0 | 2 | 0 | 0 |
| 5 | 0 | 0 | 0 | 0 | 0 | 0 |
| 4 | 0 | 0 | 0 | 2 | 0 | 2 |
| 3 | 0 | 0 | 0 | 0 | 0 | 3 |
| 2 | 0 | 0 | 0 | 0 | 8 | 2 |
| 1 | 0 | 0 | 0 | 0 | 9 | 0 |
| 0 — No Color / Very Tangled / None | 0 | 0 | 1 | 0 | 0 | 0 |
| No Answer | 0 | 0 | 0 | 0 | 0 | 0 |
| TOTAL | 17 | 8 | 17 | 8 | 17 | 7 |

- Comparative Competitive Product: Hair was relaxed and neutralized with a commercial no-lye relaxer and neutralized with the shampoo neutralizer that was provided with that no-lye relaxer. This hair was then colored with competitive hair color recommended for application after relaxing of hair.
- Color Mousse: Hair was relaxed with no-lye relaxer and neutralized and colored in one step with the neutralizer colorant compositions of the present invention.
- Further explanations of these tests are found in the specification.

FIGURE 2B: PERCENTAGE COMPARISONS FOR NEUTRALIZER COLORANT COMPOSITIONS AND COMPETITIVE COLORANT PRODUCT

| By Percent of Respondents | Color Mousse | Comparative Competitive Products | Color Mousse | Comparative Competitive Products | Color Mousse | Competitive Products |
|---|---|---|---|---|---|---|
| | Color Intensity | Color Intensity | After Neutralizing Hair Ease Of Combing/Tangles | After Neutralizing Hair Ease Of Combing/Tangles | Rate Hair Loss/Breakage | Rate Hair Loss/Breakage |
| Rating Scale | | | | | | |
| 10 | A Lot Of Color | A Lot Of Color | Very Easy | Very Easy | A Lot Of Loss | A Lot Of Loss |
| 10 | 11.8% | 37.5% | 0.0% | 0.0% | 0.0% | 0.0% |
| 9 | 58.8% | 62.5% | 76.5% | 0.0% | 0.0% | 0.0% |
| 8 | 23.5% | 0.0% | 17.6% | 25.0% | 0.0% | 0.0% |
| 7 | 5.9% | 0.0% | 0.0% | 25.0% | 0.0% | 0.0% |
| 6 | 0.0% | 0.0% | 0.0% | 0.0% | 0.0% | 0.0% |
| 5 | 0.0% | 0.0% | 0.0% | 25.0% | 0.0% | 0.0% |
| 4 | 0.0% | 0.0% | 0.0% | 25.0% | 0.0% | 0.0% |
| 3 | 0.0% | 0.0% | 0.0% | 0.0% | 0.0% | 28.6% |
| 2 | 0.0% | 0.0% | 0.0% | 0.0% | 0.0% | 42.9% |
| 1 | 0.0% | 0.0% | 0.0% | 0.0% | 47.1% | 28.6% |
| 0 | 0.0% | 0.0% | 0.0% | 0.0% | 52.9% | 0.0% |
| | No Color | No Color | Very Tangled | Very Tangled | None | None |
| No Answer | 0.0% | 0.0% | 5.9% | 0.0% | 0.0% | 0.0% |
| TOTAL | 100% | 100% | 100% | 100% | 100% | 100% |

- Comparative Competitive Product: Hair was relaxed and neutralized with a commercial no-lye relaxer and neutralized with the shampoo neutralizer that was provided with that no-lye relaxer. This hair was then colored with competitive hair color recommended for application after relaxing of hair.
- Color Mousse: Hair was relaxed with no-lye relaxer and neutralized and colored in one step with the neutralizer colorant compositions of the present invention.
- Further explanations of these tests are found in the specification.

COMPOSITIONS FOR NEUTRALIZING AND COLORING HAIR AND METHODS THEREOF

CROSS REFERENCE TO RELATED APPLICATIONS

This application is a continuation of U.S. patent application Ser. No. 10/959,758 filed Oct. 6, 2004 now U.S. Pat. No. 8,256,436, which application is a continuation-in-part application of U.S. patent application Ser. No. 10/654,233, filed Sep. 2, 2003 and issued as U.S. Pat. No. 7,874,299 on Jan. 25, 2011. The entire disclosures of these applications are incorporated by reference herein.

FIELD OF THE INVENTION

The present invention relates to processes for neutralizing relaxed hair. Still further, the present invention relates to neutralizer compositions for use on relaxed hair. Still further, the present invention also relates to a system for neutralizing relaxed hair. Yet further, the invention relates to relaxed hair neutralized by the compositions and methods disclosed herein. The present invention also relates to compositions for simultaneously coloring and neutralizing relaxed hair. Yet further, the invention relates to relaxed hair neutralized and colored by the compositions and methods disclosed herein.

BACKGROUND OF THE INVENTION

Hair is an exceedingly strong fiber. This strength is conferred primarily by disulfide bonds within the cortex of the hair fiber and by a profective cuticle layer that encapsulates the entire hair fiber. The natural degree of curliness of one's hair is largely determined by the orientation of these disulfide bonds. In order to change the physical configuration of hair, these disulfide bonds must be broken. When hair is exceedingly curly in its natural state, fairly aggressive conditions must normally be used to substantially lessen or eliminate the amount of curl. Simply put, the curlier the hair, the more curl that needs to be removed to make the hair straight and, in turn, the more disulfide bonds need to be broken to make the hair straight.

In order to straighten exceedingly curly hair, alkaline compositions must be used. These compositions differ from the thiol-based compositions used in perming in that bond breakage is achieved by hydroxide-containing compounds. Hydroxides are very strong reducing agents and the compositions in which they are formulated are highly alkaline. Accordingly, the pH of relaxer compositions is generally within the range of pH 12 to pH 14. In most circumstances, compositions for the straightening of exceedingly curly hair are termed "lye" type and "no-lye" type compositions. The relaxing process is usually combined with mechanical straightening of the hair, such as by combing, where straightening occurs through changing of the relative positions of opposite polypeptide chains.

As would be understood by one of ordinary skill in the art, under strongly alkaline conditions, such as those conferred by the application of typical relaxer compositions to hair, the disulfide bonds of cystine in hair are converted to stable, irreversible crosslinks of primarily lanthionine with some lysinoalanine. Thus, unlike when hair is reduced with thiol or bisulfite relaxers, a chemical oxidative re-linking step is unnecessary. Rather, the only step required following an alkaline relaxer is to promptly remove the relaxing composition by rinsing the hair with water, and to substantially neutralize all remaining alkaline material to avoid damage to the hair protein or skin. For this purpose, a neutral pH or acidic pH shampoo is applied to the hair to neutralize and remove residual alkaline material from the hair and scalp.

In use, after rinsing the hair of most of the excess relaxer composition, the shampoo neutralizer is applied to the hair. In order to make sure that substantially all of the alkalinity is removed from the hair, care must be taken to fully distribute the shampoo neutralizer through the hair. As such, existing methods of neutralizing relaxed hair invariably require the neutralizer shampoo composition to be massaged or kneaded into the relaxed hair.

However, when hair is in its relaxed state i.e., after straightening but before the alkalinity is removed, the fibers are easily stretched, twisted, or broken. Those skilled in the art will recognize that the studies given in the current literature clearly demonstrate that chemical treatments such as bleaching, waving, and straightening cause changes in the physical properties of hair and related fibers. Measurements of parameters such as Young's Modulus, Load-Elongation Curves and the like have shown that: (1) wet hair stretches more easily than dry hair; (2) chemically treated hair loses some of its tensile strength; (3) the amount of force required to stretch a wet chemically treated hair is lower than that required to stretch a wet, non-treated hair to the same extent; and (4) the amount of total force required to reach the breaking point in a wet, chemically treated hair is lower than that required to reach the point of breakage in wet, non-treated hair. Excessive stretching can also result in cuticle lifting and fiber splitting.

The elliptical shape of hair fibers of people of African descent, so-called "kinky" or "curly" hair is also well documented in the literature. Hair of this type tends to have a combination of areas of fairly normal cross-sectional area with intermittent bends and twists where the cross-sectional area of the hair fiber is reduced or narrowed. These areas of reduced cross-sectional area in effect create natural weak spots where mechanical forces applied to the hair are concentrated over a smaller area. Thus, persons with this type of hair are inherently more at risk of hair damage by mechanical forces applied to the hair fiber than are persons with hair of more uniform cross-sectional area. Further, excessive stretching and twisting can result in damage to or loss of hair's profective cuticle leaving the hair vulnerable to damage from heat styling, combing, and environmental effects of natural weathering. Accordingly, when a shampoo neutralizer is massaged or kneaded into the relaxed hair, hair breakage necessarily results because of the application of force to the relaxed hair from the massaging or kneading of the neutralizer shampoo into the hair. Such breakage, which may be considerable, normally occurs even when the operator is exercising care in applying the shampoo neutralizer to the relaxed hair.

Because of the significant damage resulting from the relaxation of hair, care must be taken in subsequent hair treatments. In particular, it is generally not recommended to color relaxed hair on the same day or even in the same week as the relaxer process. This is due, in part, to the fact that hair colorants are generally applied from an alkaline composition, such as those that contain ammonia or other similar materials. Such materials are generally added to colorant compositions to swell the hair and improve the penetration of the colorant into the hair fiber.

As shown in the Comparative Examples of this application and as anecdotally known to one of ordinary skill in the art, in prior art methods of neutralizing relaxed hair, the hair retains a significant amount of alkalinity even after several shampoo neutralization steps. Therefore, it is not surprising that the application of an alkaline colorant product to an alkaline hair fiber can exacerbate damage to the hair from relaxers.

Further, even when a hair color is not applied from a highly alkaline composition, the mere fact that hair relaxed and neutralized with prior art methods of neutralization retains alkalinity makes same day (or even same week) coloration substantially undesirable. For example, the additional manipulation of hair that retains alkalinity due to relaxing can cause significant breakage of the hair. Further, alkaline hair generally is more porous and less likely to retain color. Colorants generally work by absorption of the colorant moiety into the hair. If the hair is porous (as by swelling caused by excess alkalinity), the colorant will be more likely to leach from the hair after application of the color, thus leading to color loss. This color loss is, of course, undesirable. Since the alkalinity of relaxed hair will usually decrease somewhat over time, it is generally believed that it is better to not to color hair within a short time after it is relaxed, but rather wait until the relaxed hair equilibrates.

In light of the above, it would be desirable to have a process for neutralizing relaxed hair that minimizes or substantially eliminates the chance of hair damage during neutralization. Further, it would be desirable to have a process where effective neutralization of reduced hair is conferred without having to substantially manipulate the hair to apply the neutralizer composition. Still further, it would be desirable to have hair that is less damaged after relaxing and neutralizing hair. Additionally, not being able to color hair on the same day that it is relaxed is inconvenient for the customer because multiple visits to the salon are necessary to obtain the desired result. It would therefore be desirable to have the ability to relax and color hair at approximately the same time without causing significant hair damage, while also providing a satisfactory coloring process.

SUMMARY OF THE INVENTION

The present invention relates to neutralization and coloring processes for use with "lye" or "no-lye" relaxers. The present invention also relates to neutralizer mousse compositions for use on relaxed hair. Still further, the present invention relates to a system for neutralizing relaxed hair. Yet further, the invention relates to relaxed hair neutralized by the compositions and methods disclosed herein. Hair neutralized according to the methods and compositions herein exhibits at least about 10% less breakage than hair neutralized using shampoo neutralizers. The present invention also relates to neutralizer colorant compositions for use on relaxed hair. Still further, the present invention relates to a system for simultaneously neutralizing and coloring relaxed hair. Yet further, the invention relates to relaxed hair neutralized and colored by the compositions and methods disclosed herein. Hair neutralized or neutralized and colored according to the methods and compositions herein exhibits better condition than hair treated using prior art methods.

Additional advantages of the invention will be set forth in part in the description that follows, and in part will be apparent from the description, or can be learned by practice of the invention. The advantages of the invention will be realized and attained by means of the elements and combination particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

FIGS. 2a and 2b are comparisons of hair condition with the inventive "one-step" neutralizer-colorant compositions and competitive coloring products intended for use after standard relaxation with commercial relaxers and shampoo neutralizers.

DETAILED DESCRIPTION OF THE INVENTION

Figure 1:
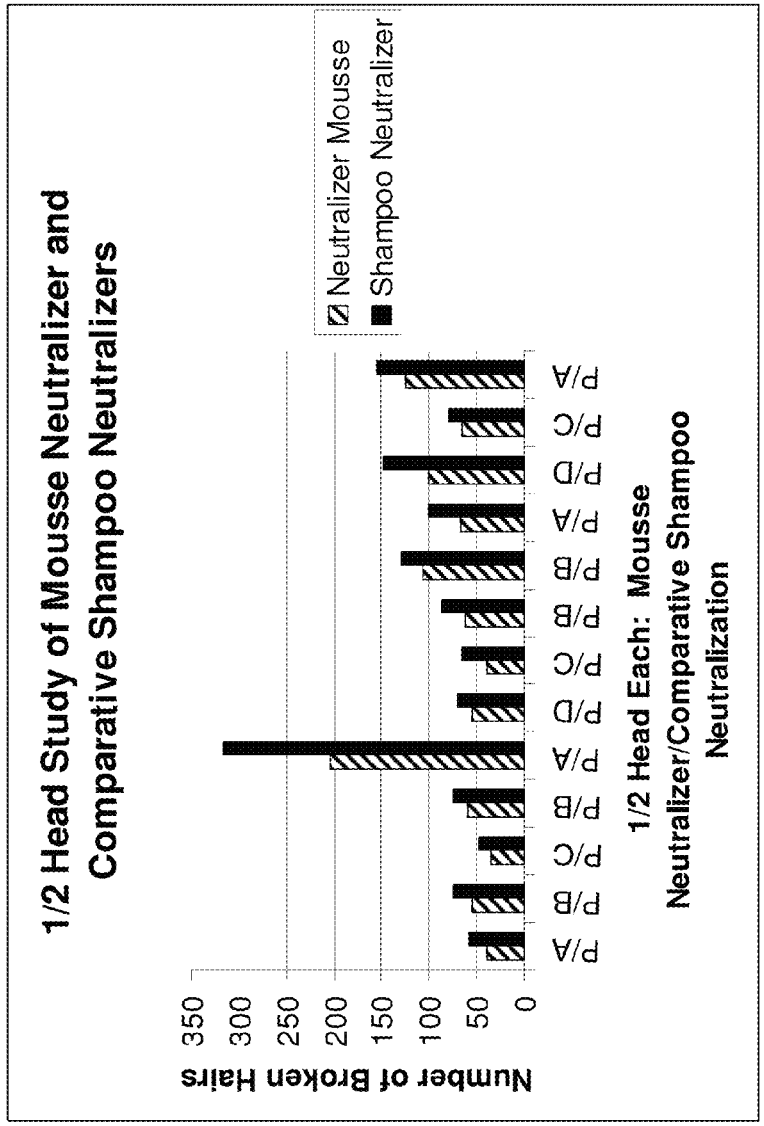
FIG. 1 is a graph of a comparison of hair damage with the neutralizer mousse compositions of the invention and comparative shampoo-type neutralizers.

The present invention can be understood more readily by reference to the following detailed description of the invention and the Examples included herein and to the Figure and its previous and following description. It is also to be understood that the terminology used herein is for the purpose of describing particular aspects only and is not intended to be limiting.

It must be noted that, as used in the specification and the appended claims, the singular forms "a," "an" and "the" include plural referents unless the context clearly dictates otherwise. Thus, for example, reference to "an acid" includes mixtures of acids.

Often ranges are expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

In the specification and in the claims that follow, reference will be made to a number of terms that shall be defined to have the following meanings:

The term "exceedingly curly hair" denotes hair that naturally exhibits a tight curl or wave pattern and will be referred to herein generally as "hair." Such hair may also be known to one of ordinary skill in the art as "kinky hair," "ethnic hair" or "curly hair."

The term "hair relaxing" as used herein refers to a treatment whereby hair is treated under a highly-alkaline pH of about greater than about pH 12 to about pH 14, wherein the composition used to relax the hair comprises a water-soluble chemical base. The composition used to relax hair is referred to herein as the "relaxing agent" or "relaxer." The compositions suitable for use herein can be "lye" and "no-lye" relaxing agents, as such materials would be known to one of ordinary skill in the art. Such compositions are discussed in detail in U.S. Pat. No. 6,562,327, the disclosure of which is incorporated herein in its entirety by this reference for its discussion of relaxing agents.

In particular, relaxing agents suitable for use herein can comprise one or more of: an alkali metal hydroxide, such as sodium hydroxide, potassium hydroxide, or lithium hydroxide; alkali earth metal hydroxide, such as calcium hydroxide, barium hydroxide and strontium hydroxide or oxides thereof capable of forming hydroxides in water; or a relatively strong organic base, such as guanidine, guanidine hydroxide or quaternary ammonium hydroxide. Yet still further, the relaxing agents can comprise liquid or cream (emulsified) compositions or a combination thereof.

"Relaxed hair" means hair that has been treated with the relaxing agent. As used herein, "relaxed hair" is hair that has not yet been neutralized.

The term "neutralize" is used herein to generally denote a post-relaxer treatment whereby residual alkalinity is eliminated from relaxed hair. A neutralizer is applied substantially immediately to the relaxed hair following completion of the relaxing step, typically after the relaxing agent has been completely removed or almost completely removed from the relaxed hair by one or more rinsing steps. "Relaxed and neutralized hair" is hair that has been subjected to hair relaxing, followed by neutralization as described further herein.

The term "color" as used herein means the application of a chemical colorant to hair for the purpose of imparting a color to the hair. The term "color" does not mean a "brightening agent" as disclosed, for example, in U.S. Pat. No. 5,293,885, the disclosure of which is incorporated in its entirety by this reference.

The term "mousse," as used herein, is equivalent to foam, and refers to the dispensed product, unless otherwise specified. The neutralizer mousse compositions of the present invention are packaged in appropriate containers equipped with the appropriate dispensers and in an appropriate manner so as to provide a product which dispenses a mousse product, the containers, dispensers and necessary techniques for this being well known to one of ordinary skill in the art.

A weight percent of a component, unless specifically stated to the contrary, is based on the total weight of the formulation or composition in which the component is included.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. For example, an effective amount of neutralizer mousse composition will depend, in part, on the amount of hair being neutralized, the strength of the relaxer composition applied and the condition of the hair prior to application of the reducing agent. Thus, it is not possible herein to specify an exact "effective amount." However, an appropriate effective amount may be determined by one of ordinary skill in the art using only routine experimentation.

The present invention relates to compositions for neutralizing relaxed hair. Yet further, the present invention relates to a system for neutralizing relaxed hair. In one aspect, the invention pertains to neutralizer mousse compositions as discussed further herein. Still further, the present invention relates to processes for neutralizing reduced hair. Yet still further, the invention relates to relaxed hair that has been neutralized with the methods and compositions herein where the hair is less damaged than relaxed hair neutralized with prior art neutralizers that require substantial manipulation of the hair upon application of the neutralizer to the relaxed hair.

In a major aspect of the present invention, the neutralizing mousse composition comprises a foam, that is, a mousse formulation. Still further, the present invention comprises a system for neutralizing hair comprising a mousse concentrate and one or more propellants. Yet still further, the present invention comprises a kit for neutralizing hair comprising a relaxing agent and a neutralizer mousse composition. Still further, the kit does not include a neutralizer shampoo composition.

The pH of the neutralizer mousse compositions of the present invention is from about pH 3.5 to about pH 8.0, or from about pH 4.5 to about pH 7.0. Still further, the pH of the neutralizer mousse compositions of the present invention can be about 3.0, 3.5, 4.0, 4.5, 5.0, 5.5, 6.0, 6.5, 7.0 or 7.5, where any value can form an upper or a lower endpoint, as appropriate.

The pH of the neutralizer mousse compositions is conferred by the presence of acid in the compositions. The acid materials that can be used to provide an acidic pH to the neutralizer compositions comprises one or more acids from the following classes: (1) organic acids—examples include, but are not limited to, citric acid, lactic acid, glutamic acid, succinic acid, EDTA acid; (2) inorganic acids—examples include, but are not limited to, hydrochloric acid, and phosphoric acid; and (3) chemical reagents capable of functioning as proton donors which by virtue of this property form acidic solutions in water.

The neutralizer mousse compositions of the present invention may optionally comprise appropriate buffering agents for the particular acids used in the compositions. Such buffering agents would be known to one of ordinary skill in the art and accordingly are not discussed in detail herein.

In one aspect, the neutralizer mousse compositions of the present invention can comprise any propellant suitable for use to provide a mousse. In a further aspect, the neutralizer mousse compositions can comprise a single propellant. In still further aspects, the neutralizer mousse compositions can comprise a mixture of two or more propellants.

In particular, the neutralizer mousse compositions of the present invention will include a propellant that serves to expel a mousse concentrate from a container, and helps form the foam character that is understood to be present in mousse compositions. The propellant used in the neutralizer mousse compositions of the present invention can be any liquefiable gas conventionally used for aerosol containers. Examples of suitable propellants include dimethyl ether and hydrocarbon propellants such as propane, n-butane and isobutane. Water insoluble propellants, especially hydrocarbons, may be used because they generally form emulsion droplets on agitation and create suitable mousse foam densities.

In one aspect, the propellant in the neutralizer mousse compositions of the present invention can comprise a compressed gas. Examples of compressed gases are nitrogen, carbon dioxide, etc., which remain as gases in the container. If the gas is soluble in the liquid neutralizer formulation, the compressed gas can be partially solubilized in the liquid formulation. As known to one of ordinary skill in the art, the pressure that results from such a product can be controlled by the amount of propellant that is solubilized in the liquid concentrate and what is left in the head space.

In a further aspect, the neutralizer mousse compositions of the present invention can comprise a liquefied propellant. They are so-called because they are gases under normal temperature and pressure but become liquids under higher atmospheric pressure. As would be recognized by one of ordinary skill in the art, liquefied propellants may be advantageous in the mousse compositions because they generally maintain a constant pressure throughout the useful life of the mousse composition by converting from a liquid state to a gaseous state as the can is depleted. This provides the user with a product that does not vary too much in its properties over the dispensing life of the product. Suitable liquefied propellants are hydrocarbons, hydrofluorocarbons and dimethyl ether. Hydrocarbons used in the personal care industry can be mixtures of isobutane, n-butane and propane. The liquefied propellants can be blended to give the desired pressure. For example, hydrocarbon A-46 is a mixture of about 15.1% by weight of propane and about 84.9% by weight of isobutane blended to give about 46 psi pressure at about 70° F. If lower pressures are desired, then the propellants can be used as is. For example, n-butane has a pressure of about 17 psi at about 70° F. and isobutane has a pressure of about 31 psi at about 70° F. which can be used without blending.

Hydrofluorocarbons may also be used in the neutralizer mousse compositions present invention. One useful hydrofluorocarbon is Dymel 152A manufactured by Dupont, (Wilmington, Del.). Dymel 152A has a pressure of about 62 psi at about 70° F. which can make it desirable for a number of mousse formulations, including the neutralizer mousse compositions of the present invention. Dymel 152A is also denser than hydrocarbons which can be an advantage when filling cans to a desired weight.

In a further aspect, the neutralizer mousse compositions of the present invention can comprise $CO_2$ as a propellant. The $CO_2$ can be used alone or in combination with another propellant disclosed herein. It has been surprisingly found that mousse compositions comprising $CO_2$ as a propellant provide superior neutralization of hair neutralized in accordance with the methods herein. Such neutralization is at least equal to or, in some cases, superior to the neutralization seen with traditional "shampoo-type" neutralizers.

Further, it has been surprisingly found that if necessary, the foam quality of the neutralizer mousse compositions having $CO_2$ as a propellant can be improved when the mousse comprises a secondary propellant, such as the hydrocarbon, ether or halocarbon propellant materials discussed elsewhere herein.

In the formulation of the neutralizer mousse compositions of the present invention, the choice and amount of propellant will be significant in determining the amount and type of foam produced. One of ordinary skill in the art would readily recognize the formulation considerations needed to obtain foams of the desired consistency. As such, the details of these formulations are not discussed in detail herein.

Amounts of propellant in the neutralizer mousse compositions of the present invention may range from about 1 to about 40% by weight of the formulation, or from about 2 to about 15% by weight, or from about 3 and about 14% by weight based on the total weight neutralizer mousse concentrate and propellant combination in the container.

In manufacturing, the liquid concentrate is generally first filled into a container which is sealed with a valve cup, followed by introduction of the propellant via pressure filling. It is also possible to do "under the cup filling" where the propellant is filled and the valve cup sealed in one step.

When the propellant is a gas, as opposed to a liquid, the amount of propellant included in the container is generally measured in pounds per square inch ("psi"). In accordance with the present invention, the amount of gaseous propellant included in the neutralizer mousse compositions can be from about 25, 50, 100, 150, 200, 250 or 300 psi, where any value can be used as an upper or a lower endpoint as appropriate and which value is limited only by the mechanical strength of the container and valving used on the dispenser.

In some aspects, a propellant suitable for use herein may have a vapor pressure that should be reduced to improve the propellant's properties for use in a mousse composition. If a propellant such as dimethyl ether includes a vapor pressure suppressant (e.g. trichloroethane or dichloromethane), for weight percentage calculations of the amount of propellant included in the neutralizer mousse composition, the amount of suppressant is included as part of the propellant.

The method of preparing neutralizer mousse compositions of the present invention is in accordance with procedures known to one of ordinary skill in the art. In such an aspect, the neutralizer mousse composition ingredients (not including the propellant) are charged into a suitable pressurizable container which is sealed and then charged with the propellant according to known methods.

Depending on the type of properties desired in the final product, the mousse can comprise one or more surfactants in varying amounts. In one aspect, a low foaming composition can be provided using a low amount of surfactant. Still further, a higher amount of surfactant can be used to provide a higher foaming mousse. Yet still further, the propellant system can be varied to affect the final properties of the dispensed foam as discussed in more detail herein.

The neutralizer mousse compositions of the present invention will typically include one or more surfactants as described above in a total amount ranging from about 0.1% to 20%, or from about 0.1% to 15% by weight based on total weight of the neutralizer mousse compositions. Still further, the amount of surfactant may be from about 0.1, 0.5, 1, 2, 3, 4, 5, 6, 7, 8, 9, 10, 12, 15, 17 or 20% by weight, where any value can form an upper or a lower endpoint as appropriate.

A wide range of surfactants generally suitable for use in hair care formulations at acidic pH's can be used in the neutralizer mousse compositions of the invention. In various aspects, nonionic, cationic, anionic, amphoteric or zwitterionic surfactants can be used either alone, or in combination, in the compositions of the present invention. Still further, the surfactant in the neutralizer mousse compositions can comprise a mixture of one or more nonionic surfactants and one or more amphoteric or zwitterionic surfactants.

Examples of nonionic surfactants that may be used in the neutralizer mousse compositions of the present invention include, but are not limited to: condensation products of aliphatic ($C_8$-$C_{18}$) primary or secondary linear or branched chain alcohols or phenols with alkylene oxides, usually ethylene oxide and generally having from about 3 to 30 ethylene oxide groups. Other suitable nonionics include esters of sorbitol, esters of sorbitan anhydrides, esters of propylene glycol, fatty acid esters of polyethylene glycol, fatty acid esters of polypropylene glycol, ethoxylated esters and polyoxyethylene fatty ether phosphates. Examples of anionic surfactants are the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to about 10 ethylene oxide or propylene oxide units per molecule, and preferably contain about 2 to 3 ethylene oxide units per molecule.

Examples of cationic surfactants that may be used in the neutralizer mousse compositions of the present invention include, but are not limited to: cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, (and the corresponding hydroxides thereof), and those materials having the CTFA designations Quaternium-5, Quaternium-31 and Quaternium-18.

Examples amphoteric and zwitterionic surfactants that may be used in the neutralizer mousse compositions of the present invention include, but are not limited to: amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from about 8 to 19 carbon atoms.

Particularly suitable surfactants for use in the neutralizer mousse compositions of the present invention are surfactants that will exhibit satisfactory foaming at the acidic or near acidic pH's exhibited by the neutralizer mousse compositions of the present invention. Examples of surfactants suitable for use in the neutralizer mousse compositions of the present invention include but are not limited to salts of lauryl sulfate or lauryl ether sulfates including but not limited to the sodium, ammonium and triethanolamine salts of these surfactants, salts of sulfosuccinates for example sodium and disodium salts, betaine surfactants such as cocamidopropyl betaine, lauramidopropyl betaine, and sulfamidobetaine, propionates for example disodium cocoamphodipropionate; amphoacetates for example disodium cocoamphodiacetate, amine oxides for example cocamidopropyl amine oxide, carboxylates such as trideceth-7 carboxylic acid, sarcosinates such as sodium lauroyl sarcosinate, and foaming protein derivatives such as TEA-cocoyl hydrolyzed protein and TEA-lauroyl hydrolyzed collagen. It should be understood by one of skill in the art that the choice of surfactant or blend of surfactants for use in the present invention is limited only by considerations of the desired foaming properties, compatibility with other mousse ingredients and long-term stability of the surfactant or surfactants at neutral or acid pH. Guidelines for surfactant use are available in the literature in such references as McCutcheon's Emulsifiers and Detergents and the actual suitability for use under the conditions of the present invention by any single surfactant or blend of surfactants can be determined by one of ordinary skill in the art without undue experimentation.

The neutralizer mousse compositions of the present invention can include one or more conditioning agents. In one aspect, the conditioning agent is of the type that would be suitable for application from an acidic pH. Still further, the conditioning agent can comprise a cationic polymeric conditioning agent such as, but not limited to, Polyquaternium-10, Polyquaternium-6, Polyquaternium-7, Polyquaternium-47, cationic guar and other water-soluble or dispersible polymeric conditioning agents.

Still further, the polymeric conditioning agent can comprise a non-ionic conditioning agent that is substantive to hair by virtue of its molecular weight, as opposed to electrostatic attraction. Such materials are well-known to one of ordinary skill in the hair care formulation art and will not be discussed in detail herein. One particularly suitable conditioning agent is AMAZE®, a corn starch-based conditioning agent available from National Starch and Chemical (Bridgewater, N.J.).

The neutralizer mousse compositions of the present invention are dispensed from the container as foams. In a significant aspect of the present invention, the neutralizer mousse compositions of the present invention are applied to hair that has been treated with relaxing agent, rinsed of the relaxer composition, but not yet neutralized. As set forth above, such hair is referred to herein as "relaxed hair."

As noted above, the neutralizer mousse compositions of the present invention have been found to provide effective neutralization when applied to relaxed hair. Surprisingly, it has been found that the neutralizing mousse compositions disclosed herein work as effectively and, in some instances, better than commercial shampoo-in neutralizers on relaxed hair. This effect was seen regardless of the propellant type used to provide the foam. Those skilled in the art can readily appreciate the fundamental problems one would expect from the use of foaming compositions for neutralizing relaxed hair.

Without being bound by theory, it is believed by the inventors herein that the formation of bubbles or lather actually ties up thin layers of the liquid neutralizing composition in the walls of the bubbles themselves. Because the acidic neutralizing compound or compounds is solublized in the same liquid tied up in the wall of each bubble, the formation of bubbles or lather is believed to have the effect of preventing the neutralizing compound from contacting the hair in all but the smallest of surface areas. Accordingly, the neutralizing agent cannot penetrate into the hair fiber to complete the task of neutralizing excess alkalinity until the bubbles have begun to burst and the liquid is freed to diffuse into the fiber. Surprisingly, it has been determined herein that the mousse-type neutralizers of the present invention are extremely effective neutralizers despite the presence of the large quantity of lather. This result was unexpected by the inventors herein.

Further, without kneading or massaging of a shampoo neutralizer into the hair, relaxed hair has been found to be significantly less likely to break due to the reduction of force applied to the hair when it is in its weakened, relaxed form. As such, it has also been surprisingly found that relaxed hair neutralized with the neutralizer mousse compositions of the present invention exhibits significantly less breakage than hair neutralized with the usually-applied shampoo neutralizer formulations.

Accordingly, one aspect of the present invention relates to a process for neutralizing relaxed hair.

In one aspect of the process for neutralizing relaxed hair, the neutralizer mousse compositions of the present invention are applied to a head of relaxed, but not yet neutralized hair. Upon application of an amount sufficient to coat the hair, the neutralizer mousse composition remains in contact with the hair for about 30 seconds, about 1 minute, about 2 minutes, about 3 minutes, about 4 minutes, about 5 minutes, about 6 minutes, about 7 minutes, about 8 minutes, about 9 minutes, or about 10 minutes or about 20 minutes. Still further, there are about 1, 2, 3, 4 or 5 separate applications of the neutralizer mousse compositions. In these aspects, the hair may or may not be rinsed prior to the further application of the neutralizer mousse compositions.

In one aspect, the neutralizer mousse composition is not massaged into the hair upon application thereof. Still further, upon application of the neutralizer mousse compositions to the hair, the mousse is lightly stroked in a downward motion directed toward the ends of the hair, as opposed to manipulating the hair in a massaging or kneading motion. This motion is similar or, in some aspects, identical to the "smoothing" action used to ensure suitable incorporation of the relaxing agent into the hair during the relaxing process. Still further, suitable incorporation of the neutralizer mousse composition into relaxed hair is accomplished with substantially no physical manipulation of the relaxed hair.

The reduction in damage seen with the methods of the present invention is manifested in there being fewer broken hair fibers in hair that has been neutralized with the neutralizer mousse compositions of the present invention, where the number of broken hair fibers is measured in comparison to the number of broken hair fibers resulting from hair that has been relaxed and then neutralized with prior art shampoo neutralizer compositions.

In accordance with this aspect, relaxed hair neutralized with the neutralizer mousse compositions of the present invention exhibits at least about 10% less breakage, or at least about 15% less breakage, or at least about 20% less breakage or at least about 25% less breakage, when compared to relaxed hair treated with shampoo-type neutralizers. Still further, hair relaxed with a no-lye relaxing agent followed by neutralization with the neutralizer mousse compositions of the present invention exhibits significantly less breakage than hair relaxed with a no-lye relaxing agent followed by neutralization with a shampoo-type neutralizer. Still further, hair relaxed with a lye relaxing agent followed by neutralization with the neutralizer mousse compositions of the present invention exhibits significantly less breakage than hair relaxed with a lye relaxing agent followed by neutralization with a shampoo-type neutralizer.

In accordance with one aspect of the present invention, the amount of alkalinity in the hair is determined by the internal pH of the hair. The internal pH is determined by soaking hair that has been relaxed and neutralized in distilled water and measuring the pH of the water after a time period. The pH of the water after soaking of the hair for the specified time is the internal pH of the relaxed and neutralized hair.

It has been found that the internal pH of the hair after application of the neutralizer mousse compositions is at or below the internal pH of hair that has been treated with prior art shampoo-type neutralizer compositions. This is surprising because, as noted above, it was thought that in order to obtain sufficient neutralization of relaxed hair it was necessary to apply substantial physical manipulation to relaxed hair and to apply a shampoo-type neutralizer composition. These compositions contain a pH indicator whereby the shampoo changed color when a certain pH was obtained. In order to obtain a full color change, it was required that the shampoo-type neutralizer be massaged or kneaded into the hair several times. As noted above, the application of such a force to the hair results in significant damage to the hair because relaxed hair is extremely breakable prior to neutralization.

In one aspect, the neutralizer mousse composition remains on the hair for a time period sufficient to provide a pH of about 11.0 or below when approximately 1 gram of relaxed hair is soaked in about 100 grams of distilled water for about 5 minutes where the water pH is measured. Still further, the neutralizer mousse composition remains on the hair for a period of time sufficient to provide a pH of about 10.0 or about 11.0 or below when approximately 1 gram of relaxed hair is soaked in about 100 grams of distilled water for about 10 minutes where water pH is measured. Still further, the neutralizer mousse composition remains on the hair for a period of time sufficient to provide a pH of 11.0 or 10.0 or below when approximately 1 gram of relaxed hair is soaked in about 100 grams of distilled water for about 20 minutes where the water pH is measured.

As would be understood by one of ordinary skill in the art, the pH of water in which the relaxed and neutralized hair has been soaked is directly related to the amount of alkaline material that remains in the hair after neutralization. A low initial water pH i.e., after about 5 minutes of soak or less, is an indicator that the relaxed hair has been significantly neutralized after application of the neutralizer mousse compositions or shampoo-type neutralizer. Further, the pH of the water soaks at longer times i.e., about 10, 15 or 20 minutes are indicative of the residual amount of alkalinity contained within the relaxed and neutralized hair fibers. As illustrated by the Examples presented below, the water soak pH's of relaxed hair treated with the neutralizer mousse compositions of the present invention are equal to or less than the water soak pH's of relaxed hair treated with prior art shampoo-type neutralizer compositions at all water soak times measured. These pH results demonstrate that the neutralizer mousse compositions of the present invention provide excellent neutralization of relaxed hair.

In one aspect, an effective amount of neutralizer mousse composition is applied to relaxed, but not yet neutralized, hair. An effective amount of neutralizer mousse composition is the amount of neutralizer that results in a pH after a 5 minute water soak of about pH 10.5 or less or about pH 10.0 or less. The conditions for the water soak are as discussed above.

While the neutralizer mousse compositions can remain in the relaxed hair for a suitable time so as to provide substantial neutralization of the relaxed hair, as would be recognized by one of ordinary skill in the art, in some aspects it may be useful to include a pH indicator in the neutralizer mousse compositions of the present invention. Such indicators allow the operator or consumer to obtain a sense of security that the neutralization process is complete by a signaling of a pH change when a suitable amount of alkalinity is eliminated from the hair. Suitable pH indicator materials are well-known in the art and are not discussed in detail herein. Once such suitable material is phenolsulfonphthalein also known as "Phenol Red." Techniques for incorporating this material into a neutralizer product are well-known to one of ordinary skill in the art and, as such, are not discussed in detail herein.

After the neutralizer mousse composition has remained on the hair for a sufficient time as defined herein or when the pH indicator signals a suitable pH change, the neutralizer mousse compositions can be rinsed from the hair. Still further, the neutralizer mousse compositions can be left in the hair. Yet still further, the hair can be styled as usual after application of the neutralizer mousse compositions of the present invention. In a further aspect, the hair can be shampooed after one or more applications of the neutralizer mousse composition of the present invention.

In one aspect, the mousse neutralizer compositions of the present invention comprise an aqueous solution of water-soluble acidic materials capable of neutralizing alkalinity on or in relaxed hair and an effective amount of a material that is suitable to provide a foam. However, one reasonably skilled in the art would recognize that the present invention can be modified to enhance the qualities of the foam obtained, the condition of the hair, and the organoleptic qualities of both the foam and the relaxed hair.

Examples of other ingredients which may be present in the neutralizer mousse compositions of the present invention include, but are not limited to: (1) viscosity adjusters and foam stabilizers like amine oxides, alkanolamides, and polymeric thickening agents; (2) pH adjusting agents and buffering agents designed to prevent age-induced changes in formula characteristics or surfactant degradation; and (3) specialty additives which impart improved organoleptic properties to the foam and/or the treated hair (examples include conditioning agents, proteins, re-fatting agents, anti-irritants, etc.) Such materials and the incorporation thereof into hair care products are well-known to one or ordinary skill in the art and, as such, is not discussed in detail herein.

In a further significant aspect, the neutralizer mousse compositions of the present invention further comprise a colorant, thereby providing a neutralizer colorant composition. In such an aspect, it has been found possible to simultaneously neutralize and color relaxed hair. To this end, the present invention provides compositions for the simultaneous neutralizing and coloring of relaxed hair, in particular, hair relaxed with "lye" or "no-lye" relaxers. Still further, the present invention provides methods of simultaneously neutralizing and coloring relaxed hair.

In one aspect, the neutralizer colorant compositions of the present invention provide excellent color to hair that has been relaxed that is substantially durable through one or more shampoos. As used herein, "substantially durable" means that the consumer will be able to discern the presence of the color imparted from the neutralizer colorant in her/his hair under normal lighting for the at least ascribed number of shampoos. It will be recognized by one of ordinary skill in the art that it is not possible to specifically identify the number of shampoos through which the color applied from the colorant neutralizer compositions of the present invention because of the different condition of hair treated with the inventive compositions. Such differing conditions are a function of one or more of the following factors: natural hair characteristics (more porous, less porous, color etc.), number and type of prior chemical treatments (including relaxers, colorants and conditioners), grooming habits (use of hot irons, regularity of shampoos, etc) and environmental quality (temperature, humidity etc., amount of UV rays). Therefore, it would be expected that the duration of the color applied from the neutralizer colorant compositions of the present invention will vary in accordance with these, as well as possibly other, factors. It is thus not possible to characterize the colorant of the present invention as "semi-permanent," "permanent" or "temporary" in relation to the duration to the colorant on the hair. Rather, in the present invention, the durability of the colorant as applied from the neutralizer colorants of the present invention are in relation to the number of shampoos through which the colorant remains substantially durable on the relaxed hair. The shampoo against which such durability is measured is a commercially available shampoo specially formulated for color treated hair.

The neutralizer colorant compositions include chemical colorants that are suitable to provide color to relaxed and neutralized hair to remain substantially durable for from about 1 to about 10 shampoos. Still further, when treated with the neutralizer colorant compositions of the present invention, treated hair retains the desired color for from about 1, 3, 5, 7, 8, 9 or 10 shampoos, where any value can form an upper or a lower endpoint, as appropriate.

The neutralizer colorant compositions of the present invention are prepared in the same or similar manners as the neutralizer mousse compositions discussed above. Such methods are disclosed in detail above.

Still further, the colorants applied from the neutralizer colorant compositions of the present invention can comprise a depositing colorant, that is, a non-lifting colorant. Yet further, the colorant applied from the neutralizer colorant compositions of the present invention is suitable for application from a substantially non-alkaline composition. In further aspects, the colorants included in the neutralizer colorant compositions of the present invention include colorants that are suitable to provide substantially durable color to relaxed hair from a composition having a pH of less than about 3.0, 3.5, 4.0, 4.5, 5.0, 5.5, 6.0, 6.5 or 7.0, where any value can form an upper or a lower endpoint, as appropriate. As used herein, the pH value of the neutralizer colorant composition (as well as the neutralizer compositions discussed above) are the measured pH of the compositions prior to application prior to application of the composition to the hair.

It is acknowledged that colorant compositions have been available where the colorant is applied from a mousse-type formulation. However, the present invention comprises a composition and methods wherein relaxed hair can be neutralized and colored by a single composition simultaneously. In particular, the prior art colorant mousse compositions are of a pH that is above that which will accomplish the neutralization of relaxed hair, that is, alkaline. Therefore, in a significant aspect of the present invention, the composition has a pH of no more than 7.0 or no more than 6.5. Still further, the compositions of the present invention are suitable for simultaneously neutralizing and providing substantially durable coloring to relaxed hair.

It will be appreciated that dyes that are normally thought of as temporary colorants may be suitable to provide a substantially durable color when applied from the neutralizer colorant compositions of the present invention. Moreover, when applied from the neutralizer colorant compositions of the present invention, colorants that are normally considered to be semi-permanent may provide a more durable color than normally expected based on the size of the colorant molecule when the same or similar colorant moieties are applied in conventional manners. This is believed to result from the fact that hair is in an exceedingly swollen state when the colorant is first applied to the hair in comparison to hair that is already not pre-swollen. Thus, a relatively larger colorant moiety can possibly enter the hair fiber than would normally be expected. Since the permanency of a hair colorant is generally related to the effectiveness of the penetration of the colorant moiety into the hair fiber, it follows that if a large colorant moiety is able to enter the fiber while the fiber is swollen from a relaxer process and the fiber is de-swollen with the moiety inside the fiber, a large color moiety could be expected to impart color to the fiber. Such large moieties are generally associated with so-called "temporary" hair colors, and it is believed that some normally "temporary" hair color moieties will provide a substantially durable hair color to hair when applied from the neutralizer colorant compositions of the present invention. Similarly, it is believed that when applied from the neutralizer colorant compositions of the present invention, semi-permanent colorants can exhibit a better durability than seen when these same colorants are applied using conventional coloring methods.

In further examples, the colorant applied from the neutralizer colorant compositions comprises one or more of: nitro dyes, anthraquinone dyes and acid dyes, oil-soluble dyes and basic dyes.

Examples of nitro dyes that may be used in the present invention include one or more of: 3,4-diaminonitrobenzene, 2,5-diaminonitrobenzene, 2-amino-5-N-β-hydroxyethylaminonitrobenzene, 2-N-β-hydroxyethylamino-5-N,N-bis-β-hydroxyethylaminonitrobenzene, 2-N-methylamino-5-N,N-bis(β-hydroxy-ethyl)aminonitrobenzene, 2-N-methylamino-5-N-methyl-β-hydroxyethylaminonitrobenzene, 2-N-β-hydroxyethylamino-5-hydroxynitrobenzene, 3-methoxy-4-N-β-hydroxyethylaminonitrobenzene, 4-nitro-3-methylaminophenoxyethanol, 2-N-β-hydroxyethylamino-5-aminonitrobenzene, 2-N-hydroxyethylamino-nitrobenzene, 3-amino-4-N-β-hydroxyethylaminonitrobenzene, 3-β-hydroxyethoxy-4-N-βhydroxyethylaminonitrobenzene, 2-amino-5-N-methylaminonitrobenzene, 2-amino-3-methylnitrobenzene, 2-N-β-hydroxyethylamino-5-β,γ-dihydroxypropoxynitrobenzene, 3-hydroxy-4-N-β-hydroxyethylaminonitrobenzene, 3-hydroxy-4-aminonitrobenzene, 2,5-N,N'-β-hydroxyethylaminonitrobenzene, 2-N-methylamino-4-o-β,γ-dihydroxypropoxynitrobenzene, 2-N-β-aminoethylamino-5-N,N-bis(β-hydroxyethyl)aminonitrobenzene, 2-N-β-aminoethylamino-4-methoxynitrobenzene and 2-N-β-aminoethylamino-5-β-hydroxyethoxynitrobenzene.

Examples of the anthraquinone dyes that may be used include, but are not limited to, one or more of: 1-amino-4-methylaminoanthraquinone and 1,4-diaminoanthraquinone.

Examples of the acid dyes include, but are not limited to, one or more of: Acid Red 27, Acid Red 51, Acid Red 18, Acid Red 92, Acid Red 94, Acid Red 52, Pigment Red 57-1, Acid Red 33, Acid Red 87, Acid Violet 9, Food Red 6, Acid Red 26, Food Red 1, Acid Red 88, Acid Orange 7, Acid Red 95, Acid Yellow 23, Food Yellow 3, Acid Yellow 73, Acid Yellow 3, Acid Yellow 40, Acid Yellow 1, Acid Yellow 36, Acid Yellow 11, Food Green 3, Acid Green 25, Solvent Green 7, Acid Green 5, Acid Green 1, Acid Green 3, Food Blue 2, Acid Blue 74, Acid Blue 5, Acid Blue 9, Acid Violet 43, Acid Black 1, Acid Blue 1, Acid Blue 3, Acid Blue 62, Acid Black 52, Acid Brown 13, Acid Green 50, Acid Orange 6, Acid Red 14, Acid Red 35, Acid Red 73, Acid Red 184 and Brilliant Black 1.

Examples of the oil-soluble dyes include, but are not limited to, one or more of: Solvent Red 49, Solvent Red 48, Solvent Red 23, Solvent Red 72, Solvent Red 73, Acid yellow 33, Solvent Green 3, Solvent Violet 13, Solvent Red 24, Solvent Orange 7, Solvent Orange 2, Solvent Yellow 5, Solvent Yellow 6 and Solvent Blue 63.

Examples of the basic dyes include, but are not limited to, one or more of: Basic Blue 6, Basic Blue 7, Basic Blue 9, Basic Blue 26, Basic Blue 41, Basic Blue 99, Basic Brown 4, Basic Brown 16, Basic Brown 17, Basic Green 1, Basic Red 2, Basic Red 12, Basic Red 22, Basic Red 51, Basic Red 76, Basic Violet 1, Basic Violet 3, Basic Violet 10, Basic Violet 14, Basic Violet 57, Basic Yellow 87 and Basic Orange 31.

The amount of dye in the neutralizer colorant compositions of the present invention can be from about 0.01 to 5.0% by weight, or from about 0.02 to 3.0% by weight based on the weight of the composition. Still further, the amount of dye in the neutralizer colorant compositions of the present invention can be from about 0.01, 0.02, 0.05, 0.1, 0.2, 0.3, 0.5, 0.7, 1.0, 1.2, 1.5, 1.7, 2.0, 2.2, 2.5, 2.7, 3.0 or 5.0% by weight of the composition, where any value can be used as an upper or a lower endpoint, as appropriate.

In one aspect, the dyes suitable for use in the present invention are direct dyes, that is, dyes that directly dye hair and do not require additional reagents to develop the color. Such direct dyes may be used singly or in combination, with a combination usage being more common.

It has been found that the color of hair treated relaxed with a relaxer, whether no-lye or lye types, and then neutralized and colored simultaneously with the neutralizer colorant compositions of the present invention provide color comparable to hair relaxed followed by a separate colorant application using a commercial colorant system (such as Reviving Colors, Carson, Soft Sheen, Chicago, Ill.). Moreover, as shown in the Examples, hair that was simultaneously neutralized and colored with the compositions of the present invention was rated as softer and judged to be in better condition than hair that was relaxed, neutralized and separately colored and neutralized.

Without being bound by theory, it is hypothesized that in the neutralizer colorant compositions and methods of the present invention, the neutralizing agent (i.e., the acidic mousse composition) and the coloring chemicals penetrate the hair simultaneously. At some time after application of the neutralizer-colorant composition, the neutralization process is completed, that is, the hair reaches a pH stasis and the remaining acidulants remain unreacted in the composition, however, it is believed that the coloring process continues as long as color continues to diffuse into the hair. When left on the hair for the appropriate time, the hair is both neutralized and colored in a simultaneous process. In one aspect, the neutralizer-colorant composition remains on the hair for at least about 1 minute, about 2.5 minutes, or about 5 minutes. Still further, the neutralizer colorant composition can remain on the hair for at least about 5, 7, 10, 12, 15, 20, 25, 30, 35, 40, 45 or 60 minutes, where any value can form an upper or a lower endpoint, as appropriate.

In yet a further aspect, multiple applications of the neutralizer colorant composition may be conducted. In such an aspect, the composition may be applied and removed, about 1, 2, 3, 4 or 5 times, with or without water rinsing between applications. When applied in multiple applications, it is generally desirable for each application to be a lesser time, however, one of ordinary skill in the art can determine the optimum application duration and number can be determined by one of ordinary skill in the art without undue experimentation.

The compositions of the present invention can have various ingredients in them such as conditioning agents, humectants, solubilizers, preservatives, antioxidants, surfactants, etc. The use of such materials in mousse products specifically, as well as hair care products specifically are well known to one of ordinary skill in the art and are not discussed in detail herein.

In one aspect, the neutralizer colorant compositions can be prepared by dispersing the colorant portions in approximately 50% of the final water content. The remaining ingredients can be incorporated into the other approximately 50% of the final water content to form a concentrate. The two portions can be blended to form a neutralizing/color concentrate that can be aerosolized to form a neutralizing color mousse. The propellant used to aerosolize the neutralizer colorant concentrate can be any of the materials discussed above with regard to the neutralizer mousse compositions as discussed above.

EXPERIMENTAL

The following Examples are put forth so as to provide those of ordinary skill in the art with a complete disclosure and description of how the compositions claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° F. or is at room temperature, and pressure is at or near atmospheric.

Each of the neutralizer mousse compositions evaluated in the Examples below were prepared using mousse concentrates MC1 or MC2 as indicated in the respective examples. The mousse dispensers were charged with the specified propellant using conventional methods.

Mousse Concentrate Formulations

A. Mousse Concentrate 1 ("MC1")

| Ingredient | Amount (g) | Source |
| --- | --- | --- |
| Water | q.s. to 100 | Deionized tap water |
| DMDM hydantoin | 0.50 | Lonza, Inc. (Fair Lawn, NJ) |
| Propylene glycol | 1.00 | Jeen Chemical (Fairfield, NJ) |
| Glutamic acid | 0.60 | Fisher Scientific (Hampton, NH) |
| Monosodium glutamate | 0.60 | Fisher Scientific (Hampton, NH) |
| Gafquat 755N | 6.00 | ISP Corp. (Wayne, NJ) |
| Monaquat TG | 1.00 | Uniqema (New Castle, DE) |
| Tween 20 | 1.00 | ICI Surfactants (Wilmington, DE) |
| Silwax WSL | 2.00 | Siltech, Inc. (Toronto, CA) |
| Phenol red | 0.01 | Pylam Dye (Tempe, AZ) |
| Fragrance | 0.40 | Intarome Fragrance (Norwood, NJ) |

B. Mousse Concentrate 2 ("MC 2")

| Ingredient | Amount (g) | Source |
|---|---|---|
| Water | q.s. to 100 | Deionized tap water |
| Methyl paraben | 0.20 | Jeen Chemical |
| Propyl paraben | 0.20 | Jeen Chemical |
| Polymer JR30M | 0.40 | Amerchol Corp. (Dow Chemical, Freeport, TX) |
| Propylene glycol | 1.00 | Jeen Chemical |
| AMAZE | 1.0 | National Starch and Chemical |
| Phenol Red | 0.01 | Pylam |
| Triethanolamine, 98% | 0.56 | Fisher Scientific |
| Citric acid | 0.41 | Fisher Scientific |
| Cocamidopropyl betaine (30%) | 13.50 | McIntyre Group (University Park, IL) |
| Disodium laureth sulfosuccinate | 5.00 | McIntyre Group |
| Polysorbate-20 | 1.00 | ICI Surfactants |
| DMDM Hydantoin | 0.40 | Lonza, Inc. |
| Fragrance | 0.25 | Intarome Fragrance |

Example 1

Procedure for Relaxing and Neutralizing Hair

Materials: DeMeo African Kinky Hair (DeMeo Brothers, Ltd.; New York)
Alkaline Hair Straightening Composition
Applicator Brush and/or Smoothing Comb
Rinse Water
Neutralizing Compositions
pH meter standardized to pH 7.0 and pH 10.0
Distilled Water
150-mL beakers Tresses of DeMeo African Kinky hair were bound at the proximal end. Each tress contained approximately one gram of hair.

For the Comparative Examples and the relaxed hair treated with the neutralizer mousse compositions of the present invention, an alkaline guanidine-based relaxer composition was applied to hair. Unless otherwise specified, all examples were treated with a relaxer composition comprising a 1:1 mixture of 8% by weight $Ca(OH)_2$ cream base and a 12% by weight guanidine carbonate cream base. After thorough mixing of the compositions, an applicator brush was used to apply the relaxer composition to African Kinky hair and timing was begun. The relaxer composition remained on the hair for 20 minutes. During that time, the applicator brush was used to smooth the hair twice (once 5-min after initial application and again 15-min after the initial application). After 20 min, excess relaxer was rinsed from the tress using tap water. The tress was very lightly blotted with fingertips to remove excess water. The tress was then ready for immediate treatment with neutralizing composition(s).

For the Comparative Examples, the identified shampoo-type neutralizer compositions were applied to the hair and allowed to remain in contact with the hair as directed by the manufacturer. In the case of commercial shampoo neutralizer products, the tresses were repeatedly shampooed until the lather formed during shampooing no longer turned pink.

In the case of the neutralizing mousse compositions of the present invention, unless otherwise specified, mousse was sprayed onto hair in an amount sufficient to saturate the hair and allowed to remain on the hair for 1 minute. The hair was not massaged or kneaded while the neutralizer mousse composition was on the hair. The pH of all neutralizer mousse compositions was between pH 4.0 and 6.0.

When noted, the neutralizer mousse composition was applied in multiple applications. All tresses were rinsed with water after each application of neutralizing composition. After the final application of neutralizing composition, each tress was rinsed with distilled water and blotted.

Example 2

Determination of the Internal pH of Relaxed and Neutralized Hair

To determine the internal pH of the hair, relaxed and neutralized tresses were placed in a beaker containing 100 grams of distilled water and a standardized pH electrode. The pH of the distilled water soak was recorded at 5 minute intervals for 5 to 20 min.

Example 3 pH Results for Neutralization of Hair with Neutralizer Mousse Compositions Prepared from MC1

Neutralizer mousse compositions were prepared from MC1 as set out above. Mousse formulations conforming to various neutralizer mousse compositions of the present invention were prepared using conventional filling techniques with the propellants as specified.

Tresses were relaxed and neutralized with the neutralizer mousse compositions of the present invention according to the procedure in Example 1. The pH results are as follows:

| | | pH of water soak after, | | | |
|---|---|---|---|---|---|
| Sample | Propellant | 5 min | 10 min | 15 min | 20 min |
| 010-1 | A-70 at 6.0 wt % | 10.50 | 10.77 | 10.80 | 10.88 |
| 010-2 | A-46 at 6.0 wt % | 10.48 | 10.73 | 10.84 | 11.01 |
| 010-3 | 134a at 6.0 wt % | 9.75 | 10.17 | 10.26 | 10.30 |
| 010-4 | $CO_2$ at 5.0 wt % | 8.40 | 8.76 | 9.20 | 9.21 |

The above results demonstrate that neutralizer mousse compositions of the present invention provide significant neutralization to relaxed hair.

Example 4

Comparative Examples

Determination of pH of Hair Relaxed and Neutralized with Commercial Relaxer Formulations A number of commercially available neutralizer products typically recommended for use after a relaxer treatment were tested on hair treated with the guanidine-type relaxer specified above in Example 1. The neutralizer compositions were as supplied in commercially available hair relaxer products. Each product was evaluated on two occasions so that the reproducibility of the results was clearly demonstrated.

| Product/Mfr | 5 min pH | 10 min pH | 15 min pH | 20 min pH |
|---|---|---|---|---|
| Optimum Care (Soft Sheen Carson) | 9.69 | 9.85 | 9.98 | n/d |
| Optimum Care (Soft Sheen Carson) | 9.56 | 9.88 | 9.99 | 10.15 |
| Synthesis III (Soft Sheen Carson) | 9.66 | 9.88 | 9.96 | 10.05 |
| Synthesis III (Soft Sheen Carson) | 9.62 | 9.9 | 9.98 | 10.19 |
| Gentle Treatment (Johnson Products) | 9.78 | 10.19 | 10.41 | n/d |
| Gentle Treatment (Johnson Products) | 9.32 | 10.28 | 10.48 | 10.57 |
| Dark & Lovely (Soft Sheen Carson) | 9.84 | 10.35 | 10.46 | n/d |
| Soft-n-Beautiful (Pro-Line Corp) | 9.97 | 10.17 | 10.28 | n/d |
| IsoPlus (JM Products) | 9.82 | 9.99 | 10.56 | 10.91 |
| Elasta QP (Elasta Products) | 9.83 | 10.23 | 10.38 | 10.55 |
| Clariol Textures (Clairol) | 10.44 | 10.52 | 10.62 | 10.71 |

"n/d" means data for this time point were not obtained.

Example 4

Effect of Extended Neutralization Times and Multiple Treatments on pH of Relaxed and Neutralized Hair

| Sample | | | pH of water soak after, | | |
|---|---|---|---|---|---|
| | | | 5 min | 10 min | 15 min |
| EXTENDED TREATMENT TIMES NEUTRALIZER MOUSSE COMPOSITIONS WITH MC2 | | | | | |
| 108-1 | $CO_2$ at 50 psi | 5 MIN | 9.7 | 10.2 | 10.31 |
| 108-2 | $CO_2$ at 100 psi | 5 MIN | 10.31 | 10.61 | 10.73 |
| 108-3 | $CO_2$ at 150 psi | 5 MIN | 9.65 | 10.73 | 10.81 |
| MULTIPLE TREATMENTS NEUTRALIZER MOUSSE COMPOSITIONS WITH MC2 | | | | | |
| 118-1 | $CO_2$ Saturation & Purge | First | 9.59 | 10.27 | 10.29 |
| 118-2 | $CO_2$ Saturation & Purge | Second | 9.31 | 9.68 | 9.7 |
| 118-3 | $CO_2$ Saturation & Purge | Third | 8.86 | 9.17 | 9.54 |
| 119-2 | $CO_2$ Saturation & Purge | First | 9.91 | 10.45 | 10.48 |
| 119-3 | $CO_2$ Saturation & Purge | Second | 9.9 | 10.14 | 10.21 |
| 119-4 | $CO_2$ Saturation & Purge | Third | 8.81 | 9.1 | 9.34 |

This example shows that extended treatment times and multiple applications of the neutralizer mousse compositions of the present invention can lower the internal pH of the hair.

Example 5

Effect of Propellant Type and Amount on Neutralization Effectiveness

| Sample | NEUTRALIZER MOUSSE COMPOSITIONS TYPE | 5 min | 10 min | 15 min |
|---|---|---|---|---|
| NEUTRALIZER MOUSSE COMPOSITIONS prepared with MC1 | | | | |
| 008-1 | MC1; A-70 propellant at 6.0 wt % | 10.5 | 10.77 | 10.8 |
| 008-2 | MC1; A-46 propellant at 6.0 wt % | 10.48 | 10.73 | 10.84 |
| 008-3 | MC1; 134a propellant at 6.0 wt % | 9.75 | 10.17 | 10.26 |
| 008-4 | MC1; $CO_2$ propellant at 5.0 wt % | 8.4 | 8.76 | 9.2 |
| NEUTRALIZER MOUSSE COMPOSITIONS prepared with MC1 | | | | |
| 108-1 | MC2; with $CO_2$ at 50 psi | 10.44 | 10.82 | 10.81 |
| 108-2 | MC2; with $CO_2$ at 100 psi | 9.61 | 10.46 | 10.64 |
| 108-3 | MC2; with $CO_2$ at 150 psi | 10.41 | 10.82 | 10.96 |
| 129-1 | MC2; $CO_2$ saturation and purge | 9.61 | 9.66 | 9.69 |
| 129-1 | MC2; $CO_2$ saturation and purge | 9.74 | 9.95 | 9.97 |
| 129-1 | MC2; $CO_2$ saturation and purge | 9.41 | 9.73 | 9.88 |

In this example, hair was relaxed for 20 min with a mixture of 8% $Ca(OH)_2$ cream base (60 grams) and 12% guanidine carbonate cream base (40 grams). After rinsing the relaxer composition from the hair, each tress was coated with mousse. The mousse was allowed to remain on the hair for 1 min. After 1 min the tress was thoroughly rinsed with tap water and blotted prior to further testing.

This example shows that various propellant types may be used in the neutralizer mousse compositions of the present invention to provide effective neutralization.

Example 6

Effect of Propellant on Neutralization Effectiveness

| Sample | Propellent | pH of water soak after | | | |
|---|---|---|---|---|---|
| | | 5 min | 10 min | 15 min | 20 min |
| 127-1 | $CO_2$ | 9.4 | 10.33 | 10.49 | 10.46 |
| 128-1 | 5 wt % $CO_2$, 1X | 8.81 | 9.83 | 9.87 | 9.92 |
| 129-1 | AB-46 | 10.65 | 10.67 | 10.7 | 10.82 |
| 130-1 | 152A | 10.3 | 10.46 | 10.67 | 10.69 |
| 139-3 | 5 wt % P-134a, 1X | 10.31 | 10.58 | 10.89 | 10.91 |
| 140-1 | 5 wt % P134a/$CO_2$, 1X | 10.33 | 10.55 | 10.6 | 10.63 |
| 127-2 | $CO_2$ | 8.32 | 9.18 | 9.2 | 9.23 |
| 128-2 | 5 wt % $CO_2$, 2X | 8.29 | 8.73 | 9.09 | 9.19 |
| 129-2 | AB-46 | 9.09 | 10.11 | 10.14 | 10.16 |
| 130-2 | 152A | 9.43 | 9.99 | 10.4 | 10.44 |
| 139-4 | 5 wt % P-134a, 2X | 10.28 | 10.54 | 10.68 | 10.77 |
| 140-2 | 5 wt % P134a/$CO_2$, 2X | 9.64 | 9.99 | 10.17 | 10.38 |
| 127-3 | $CO_2$ | 8.51 | 9.29 | 9.47 | 9.5 |
| 128-3 | 5 wt % $CO_2$, 3X | 8.23 | 8.53 | 8.8 | 8.78 |
| 129-3 | AB-46 | 8.65 | 9.1 | 9.47 | 9.51 |
| 130-3 | 152A | 8.8 | 10.27 | 10.32 | 10.34 |
| 139-5 | 5 wt % P-134a, 3X | 9.88 | 10.31 | 10.52 | 10.52 |
| 140-3 | 5 wt % P134a/$CO_2$, 3X | 8.99 | 9.64 | 9.85 | 9.92 |

This example shows that different propellant types can provide effective neutralization to relaxed hair. 1×, 2× and 3× indicates number of times the neutralizer mousse composition was applied to the neutralized hair.

HFC 134a is supplied by DuPont Corporation (Wilmington, Del.). A-46 Propellant is supplied by Aeropres Corporation (Shreveport, La.). AB-46 is supplied by Diversified CPC Intl. (Chinnanon, Ill.). P-134a is supplied by Technical Propellents Inc. (Ponca City, Okla.).

Example 7

Effect of Mixed Propellant System on Neutralization Effectiveness

| | | pH of deionized water soak at | | | |
|---|---|---|---|---|---|
| Sample | Propellent | 5 min | 10 min | 15 min | 20 min |
| NEUTRALIZER MOUSSE COMPOSITIONS MADE WITH MC2 | | | | | |
| 157-1 | 2% A-46 & 100 psi $CO_2$ | 9.61 | 9.8 | 10.6 | 10.61 |
| 158-1 | 1% A-46 & 100 psi $CO_2$ | 9.26 | 9.82 | 10.38 | 10.39 |
| 157-2 | 2% A-46 & 100 psi $CO_2$ | 8.83 | 9.23 | 9.24 | 9.23 |
| 158-3 | 1% A-46 & 100 psi $CO_2$ | 8.83 | 9.21 | 9.3 | 9.3 |

Neutralization data are based on three 1-min applications of mousse to relaxed hair. This example shows that a mixed propellant system neutralizer mousse compositions provides excellent neutralization of relaxed hair. The hair was rinsed between applications.

Example 8

Neutralization Effectiveness of MC2 Dispensed from Spray-Type Mousse Containers

| | pH of water soak after, | | | |
|---|---|---|---|---|
| Sample | 5 min | 10 min | 15 min | 20 min |
| 164-1 | 10.27 | 10.35 | 10.64 | 10.66 |
| 164-2 | 9.46 | 9.83 | 10.09 | 10.12 |
| 164-3 | 9.15 | 9.7 | 9.88 | 9.99 |
| 164-4 | 9.77 | 10.39 | 10.64 | 10.7 |

(1) Samples were packaged in aerosol cans equipped with spray-type nozzles rather than mousse nozzles. P-134a was used to aerosolize the above samples and the last digit in the sample code represents the percentage of propellant.

The above data show that the neutralizer mousse compositions of the present invention effectively neutralize relaxed hair when dispensed from spray-type mousse containers.

Example 9

Neutralizer Effectiveness of MC2 Neutralizer Mousse Formulation Having Mixed $CO_2$-Butane Propellant System

| | pH of water soak after, | | | |
|---|---|---|---|---|
| Sample | 5 min | 10 min | 15 min | 20 min |
| 011-1 | 8.86 | 9.21 | 9.47 | 9.49 |
| 011-2 | 9.63 | 10.28 | 10.53 | 10.53 |

The neutralizer mousse compositions of this example had a propellant of 2.0% butane and carbon dioxide which was filled via impact gassing.

Example 10

Evaluation of Hair Breakage with Hair Relaxed with No-Lye Relaxers and Neutralized with Neutralizer Mousse Compositions and Competitive Shampoo Neutralizers No-Lye Relaxer Products Used in Study (Type of Neutralizer Supplied with Product)

A. Dark & Lovely—L'Oreal S.A., New York, N.Y.—(shampoo neutralizer)

B. Optimum—Soft Sheen, Chicago, Ill.—(shampoo neutralizer)

C. Soft & Beautiful—Alberto-Culver, Melrose Park, Ill.—(shampoo neutralizer)

D. Precise—Wella Group, Woodland Hills, Calif.—(shampoo neutralizer)

E. P-Profectiv—Strength of Nature, Savannah, Ga.—(neutralizer mousse)

The neutralizer mousse in the Profectiv product has the following formulation (sources as in Example 1):

| INGREDIENT | WT % |
|---|---|
| Part A | |
| Water | q.s. to 100 |
| Preservative | 1.00 |
| Polymer JR30M | 0.40 |
| AMAZE | 1.00 |
| Part B-Premix | |
| Water | 1.00 |
| Triethanolamine, 88% | 0.56 |
| Part C-Premix | |
| Water | 1.00 |
| Phenol Red (Indicator) | 0.01 |
| Part D-Premix | |
| Water | 1.00 |
| Citric Acid, anhydrous | 0.41 |
| Part E | |
| Cocamidopropylbetaine, 30% | 6.75 |
| Mackinate EL | 2.50 |
| Part F-Premix | |
| Polysorbate 20 | 1.00 |
| Fragrance and natural extracts | 0.40 |

The premix ingredients were mixed together to form a mousse concentrate. The mousse concentrate was charged into a mousse dispenser along with a mixture of carbon dioxide at 100 psi and A-46 propellant at 2% by weight.

The salon evaluator parted a head of hair into two sections down the middle. The left side of the head was defined and then one of either of the no-lye relaxers denoted A, B, C or D was applied to one side of the half head. Each other half head had a single no-lye relaxer applied to the head (Profectiv, Strength of Nature LLC, Savannah, Ga.). In the relaxer application and neutralizing process, care was taken to keep products separate on each side of the head. After completion of the relaxing and neutralizing steps, the salon evaluator took care to collect broken hair that had fallen out from each side of head. Broken hair from each side of the head was then placed in a marked container. After broken hair naturally dried inside the marked container, the evaluator counted broken hair from each half head side. The hair count is shown in Table 1.

TABLE I

COMPARISON OF HAIR RELAXED WITH NO LYE RELAXERS AND TREATED WITH SHAMPOO-TYPE NEUTRALIZER AND NEUTRALIZER MOUSSE COMPOSITIONS

| Head Number | Type of relaxer per each half of head | Number of Broken Hairs: Neutralizer Mousse Composition | Number of Broken Hairs: Shampoo Neutralizers | % Decrease in Number of Broken Hairs with Neutralizer Mousse Composition |
|---|---|---|---|---|
| 1 | P/A | 39 | 58 | −33% |
| 2 | P/B | 55 | 75 | −27% |
| 3 | P/C | 35 | 47 | −26% |
| 4 | P/B | 60 | 75 | −20% |
| 5 | P/A | 204 | 316 | −35% |
| 6 | P/D | 55 | 70 | −21% |
| 7 | P/C | 40 | 65 | −38% |
| 8 | P/B | 62 | 87 | −29% |
| 9 | P/B | 107 | 130 | −18% |
| 10 | P/A | 67 | 100 | −33% |
| 11 | P/D | 100 | 147 | −32% |
| 12 | P/C | 66 | 79 | −16% |
| 13 | P/A | 125 | 155 | −19% |
| TOTAL | | 1015 | 1404 | −28% |

From the above data, which are presented in graphic form in FIG. 1, it is apparent that hair relaxed with no-lye relaxer that is neutralized using a neutralizer mousse composition of the present invention exhibits significantly less breakage than hair on the same head that has been relaxed with a no-lye relaxer and neutralized with a shampoo-type neutralizer product. Moreover, the evaluators consistently rated the neutralizer mousse composition treated hair as shinier and softer than hair treated with shampoo-type neutralizers. Further, the evaluators recognized that hair neutralized with the neutralizer mousse compositions of the present invention had increased tensile strength. These results demonstrate that the neutralizer mousse compositions of the present invention provide results that are superior to neutralization with competitive shampoo-type neutralizer compositions.

Example 11

Application of the Neutralizer Colorant Compositions to Hair

The hair was relaxed with a no-lye relaxer (Profectiv, Strength of Nature) using the instructions provided by the manufacturer. At the end of the relaxing step, the hair was rinsed to remove excess relaxer residue and lightly blotted to remove excess water. The neutralizing/color mousse was foamed into the relaxed hair and allowed to remain in contact with the hair either for 5 or 20 minutes as indicated followed by rinsing.

Comparison of Hair Treated with Neutralizer Colorant Compositions and Neutralizer Shampoos Followed by Separate Coloring Agents Two shades of Neutralizing/Colorant Mousse selected were selected: Black (Sample #04051203) and Brown Auburn (Sample #04042902). These two samples were aerosolized at IKI Manufacturing (Edgerton, Wis.). The two aerosolized samples had been stored for 10 wks at 45° C. as a part of an ongoing stability study of the neutralizing/color mousses. (These two shades were selected for testing because the dyes used to prepare them also appears on the labels of the commercial formulations against which the inventive neutralizer colorant compositions were tested.)

A. Neutralizing Color Mousse for Delivery of Black Color to Relaxed Hair

| Ingredient/Supplier | INCI Name | wt % |
|---|---|---|
| Cocamidopropyl betaine, 30% (McIntyre Group) | Cocamidopropyl betaine | 6.75 |
| Mackenate EL (Essential Ingredients) | Disodium laureth sulfosuccinate | 2.5 |
| Disperse Violet #1 (J. H. Lowenstein & Sons) | Disperse Violet #1 (CI61100) | 2.75 |
| HC Blue #2CP (J. H. Lowenstein & Sons) | HC Blue #2 | 1.8 |
| Polymer JR 30M (Amerchol) | Polyquaternium-10 | 0.40 |
| AMAZE (National Starch) | Modified corn starch | 1.0 |
| Citric acid (Ajinamoto) | Citric acid | 0.7 |
| Disperse Black #9 (J. H. Lowenstein & Sons) | Disperse Black #9 | 0.25 |
| HC Yellow #4 (J. H. Lowenstein & Sons) | HC Yellow #4 | 0.20 |
| Sodium citrate (Universal Preserv-a-Chem) | Sodium citrate | 1.0 | q.s. to 100%: water, preservative, fragrance, solubilizer, humectant and antioxidant.

Neutralizing Color Mousse for Delivery of Warm Auburn Color to Relaxed Hair

| Ingredient/Supplier | INCI Name | wt % |
|---|---|---|
| Cocamidopropyl betaine, 30% (McIntyre Group) | Cocamidopropyl betaine | 6.75 |
| Mackenate EL (McIntyre Group) | Disodium laureth sulfosuccinate | 2.5 |
| Polymer JR 30M (Amerchol) | Polyquaternium-10 | 0.40 |
| AMAZE (National Starch) | Modified corn starch | 1.00 |
| Citric acid (Ajinamoto) | Citric acid | 0.70 |
| D&C Orange #4 (Pylam) | D&C Orange #4 (CI15510) | 0.12 |
| D&C Red #33 (Pylam) | D&C Red #33 (CI 17200) | 1.00 |
| Ext. D&C Violet #2 (Pylam) | Ext. D&C Violet #2 (CI 60730) | 0.20 |
| Sodium citrate (Universal Preserv-a-Chem) | Sodium citrate | 1.00 | q.s. to 100%: water, preservative, fragrance, solubilizer, humectant and antioxidant.

Two samples of a commercial relaxer (Dark & Lovely No-Lye Mix) and commercial semi-permanent hair colors (Reviving Colors Radiant Black and Spiced Auburn) whose instructions state that they can be used consecutively were obtained for comparison testing.

Preparation of Relaxed Hair

Tresses of relaxed hair were prepared by applying Dark & Lovely relaxer (Super strength) to DeMeo Light Brown European Hair (DeMeo Brothers, Ltd., New York, N.Y.) for 20 min. The relaxed tresses were then rinsed with tap water to remove excess relaxer cream from the hair and blotted lightly to remove excess moisture. Tresses of relaxed hair were prepared immediately prior to use.

Tresses Treated with Reviving Colors Semi-Permanent Hair Color:

Tresses of relaxed hair were shampooed three times with the Dark & Lovely Color Signal Neutralizing shampoo that was included in the Dark & Lovely relaxer kit. After rinsing the third shampoo treatment from the hair, tresses were rinsed between shampoo applications as directed in the kit instructions. After rinsing, the third shampoo treatment from the hair, the excess water was blotted from each tress. As instructed in the Reviving Colors Semi-permanent color kits, each relaxed/neutralized tress was shampooed once with the Color Care shampoo included in the Reviving Colors kit. The shampooed tresses were then blotted to remove excess water and the color base from the Reviving Colors kit was applied to the tresses. The color base was allowed to remain on the tresses for 30 min. after which each tress was rinsed with tap water to remove excess color base. The dyed tresses were then blotted, lightly rinsed with distilled water, blotted, and transferred to a beaker containing 100 grams of distilled water. The pH of the distilled water soak was monitored at 5 min intervals for 20 min.

Tresses Treated with Neutralizer Colorant Compositions

Each of the two Neutralizing/Color mousse of Examples 11A and 11B was foamed directly onto the relaxed hair and allowed to remain in contact with the hair for one minute. The tresses were then rinsed with water, blotted, and a second application of neutralizing/color mousse was made. The second application of mousse was allowed to remain on the hair for 20 min after which the tress was rinsed with tap water to remove excess mousse. The dyed tresses were then blotted, lightly rinsed with distilled water, blotted, and transferred to a beaker containing 100 grams of distilled water. The pH of the distilled water soak was monitored at 5 min intervals for 20 min.

In a second set of tresses, the procedure in the preceding paragraph was modified slightly. The inventive neutralizer colorant mousse was foamed directly onto the relaxed hair and allowed to remain in contact with the hair for one minute. The tresses were then rinsed with water, blotted, and a second application of neutralizing/color mousse was made. The second application of mousse was allowed to remain on the hair for 5 min after which the tress was rinsed with tap water to remove excess mousse. A third, and fourth application of mousse was smoothed onto the hair, each remaining on the hair for 5 min. After each application the tress was rinsed with tap water to remove excess mousse. The fourth and final application of mousse was allowed to remain on the hair for 5 min so that the total time of exposure was equal to the 21 min described in the preceding paragraph. The dyed tresses were then blotted, lightly rinsed with distilled water, blotted, and transferred to a beaker containing 100 grams of distilled water. The pH of the distilled water soak was monitored at 5 min intervals for 20 min.

The data supporting the following observations can be found in Table 1. The data given for Reviving Colors-treated hair represent duplicate sets of tresses prepared using the same procedure. The data given for the neutralizer colorant compositions represents one set of tresses (for each color) prepared using a 1 min and a single 20 min application of mousse and a second set of tresses using the 1 min application followed by four separate 5-min treatments.

All of the tresses yielded data in the near neutral range of pH.

The tresses of hair were evaluated for softness immediately after rinsing the color compositions from the hair but before the distilled water soak used to obtain pH data. Subjective evaluations of all of the tresses clearly showed that the tresses treated with the inventive neutralizer colorant compositions were noticeably softer and silkier to the touch than those treated with Reviving Colors. The Reviving Colors-treated tresses felt "raspy" with more tangles than the tresses treated with the inventive neutralizer colorant compositions.

An attempt was made to subjectively evaluate the degree of color leaching that occurred during the distilled water soak. There was no noticeable difference in the intensity of the color leached from the tresses treated with either of the black shades. There was a slight difference in the actual shade of color leached from the tresses treated with the Spiced Auburn and Brown Auburn shades. Spiced Auburn yielded a more yellow-red soak solution and the Brown Auburn yielded a more orange-red soak solution. This difference in shade made any meaningful comparison of amount of color leaching difficult to obtain.

TABLE J

Neutralization Data Obtained For Relaxed and Dyed Tresses of DeMeo Hair (From Example 21)

| Sample | Hair Color Used | pH of Distilled Water Soak After | | | | |
|---|---|---|---|---|---|---|
| | | 0 min | 5 min | 10 min | 15 min | 20 min |
| 124-1 | Radiant Black # (Comp) (Carson Soft-Sheen) | 4.92 | 5.89 | 6.54 | 7.28 | 7.57 |
| 125-1 | Radiant Black # (Comp) (Carson Soft-Sheen) | 4.92 | 7.21 | 7.46 | 7.57 | 7.82 |
| 125-2 | Spiced Auburn # (Comp) (Carson Soft-Sheen) | 4.92 | 5.95 | 6.65 | 7.4 | 7.64 |
| 126-1 | Spiced Auburn # (Comp) (Carson Soft-Sheen) | 4.92 | 7.28 | 7.43 | 7.68 | 7.8 |
| 126-2 | Black #04051203 | 4.92 | 5.5 | 6.39 | 7.47 | 7.75 |
| 127-1 | Black (1) #04051203 | 4.92 | 5.98 | 6.74 | 7.24 | 7.42 |
| 127-2 | Brown Auburn #04042902 | 4.92 | 6.1 | 6.75 | 7.56 | 7.64 |
| 128-1 | Brown Auburn (1) #04042902 | 4.92 | 6.34 | 7.04 | 7.42 | 7.6 |

All tresses were relaxed with Dark & Lovely No-Lye Mix Super relaxer before treatment with hair color.

Example 12

Neutralizer Colorant Compositions Whole Head Test

A salon full head test was conducted. Hair treatments were applied by experienced salon professionals; ratings were also conducted by such professionals. The results are provided in FIGS. 2A and 2B.

Referring to these Figures, columns denoted "Comparative Competitive Products," reflect the ratings of whole head tests where the hair was first relaxed with a commercial relaxer product and neutralized with the shampoo neutralizer provided with that product according to label instructions. The commercial products used were: Profectiv, Silk 2 No-lye relaxer and Silk 2 lye relaxer (Silk 2 is a product of Searles Corp., Atlanta, Ga.). After completion of neutralization, the whole head was colored with a commercial colorant indicated to be suitable for use on relaxed hair (Reviving Colors). For the columns denoted "Color Mousse," whole heads relaxed with a commercial no-lye relaxer (the relaxer portion of the Profectiv product mentioned previously) were neutralized with the neutralizer colorant compositions of the present invention. The neutralizer colorant composition was applied to the whole head of relaxed hair and kept in contact with the hair for a period of time judged by the operator to result in a good coloring to the hair.

As evident from FIGS. 2A and 2B, hair neutralized and colored in one step with the neutralizer colorant compositions of the present invention were comparable (if not better) rated than hair treated in accordance with standard methods. Surprisingly, the hair color of hair treated with the inventive compositions was rated as almost as good as hair colored in a separate step using the post-relaxer/neutralizer process of existing products. Further, hair treated with the inventive compositions was generally rated as easier to comb and having less breakage.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A composition for simultaneously neutralizing and coloring relaxed hair comprising:
   a. a mousse concentrate comprising water, an acid and a surfactant;
   b. one or more propellants; and
   c. a colorant suitable for imparting to hair a substantially durable color to hair, wherein the composition has a pH of no more than 7.0 when first applied to the relaxed hair wherein the composition is for simultaneously neutralizing and coloring relaxed hair.

2. The composition of claim 1, wherein the colorant comprises one or more of: nitro dyes, anthraquinone dyes and acid dyes, oil-soluble dyes and basic dyes.

3. The composition of claim 1, wherein the amount of dye in the neutralizer colorant compositions of the present invention can be from about 0.01 to 5.0% by weight.

4. The composition of claim 1, wherein the one or more propellants comprise one or more of: a hydrocarbon, a hydrofluorocarbon or dimethyl ether.

5. The composition of claim 1, wherein the one or more propellants comprises carbon dioxide, wherein the pressure of the propellants in the container is from about 50 to about 200 psi.

6. A kit comprising the composition of claim 1 and a relaxing agent.

7. The kit of claim 6, wherein the relaxing agent comprises a no lye relaxer.

8. The kit of claim 6, wherein the relaxing agent comprises a lye relaxer.

* * * * *